US009066790B1

(12) United States Patent
Fisher (10) Patent No.: US 9,066,790 B1
(45) Date of Patent: Jun. 30, 2015

(54) ORTHOPEDIC TOE DEVICE

(71) Applicant: David Newman Fisher, San Francisco, CA (US)

(72) Inventor: David Newman Fisher, San Francisco, CA (US)

( * ) Notice: Subject to any disclaimer, the term of this patent is extended or adjusted under 35 U.S.C. 154(b) by 226 days.

(21) Appl. No.: 13/763,032

(22) Filed: Feb. 8, 2013

Related U.S. Application Data (60) Provisional application No. 61/597,245, filed on Feb. 10, 2012.

(51) Int. Cl.
*A61F 5/00* (2006.01)
*A61F 5/01* (2006.01)

(52) U.S. Cl.
CPC ...................................... *A61F 5/019* (2013.01)
USPC ................................................ 602/30; 602/23

(58) Field of Classification Search
CPC ............................ A61F 5/019; A01B 12/1006
USPC ................ 602/5, 23, 30; 128/892–894; 5/624
See application file for complete search history.

(56) References Cited

U.S. PATENT DOCUMENTS

| 1,787,398 | A | * | 12/1930 | Sidgreaves | 602/30 |
| 2,932,295 | A | * | 4/1960 | Fisher | 602/30 |
| 3,094,985 | A | * | 6/1963 | Frances | 602/30 |
| 3,196,869 | A | * | 7/1965 | Scholl | 602/30 |
| 3,211,142 | A | * | 10/1965 | Johannes | 602/30 |
| 2006/0069334 | A1 | * | 3/2006 | Moskowitz | 602/5 |

* cited by examiner

*Primary Examiner* — Michael Brown
(74) *Attorney, Agent, or Firm* — Rankin, Hill & Clark LLP (57) ABSTRACT

A hammer toe treatment device to help uncurl a hammer toe and protect the toe including a base pad configured to extend in a neck portion of the between the toe mound and tip of the toe. The base pad including an arcuate top surface extending in the direction of the hammer toe and configured to produce a straightening force against the toe. The pad including a bottom surface generally opposite to the top surface that includes a generally flat surface configured to engage a shoe insole when the shoe is worn. The base pad further including a tubular toe sleeve fixed relative to the base pad and extending forwardly along a sleeve axis from a reward toe opening. The sleeve axis extending at a sleeve angle relative to the bottom surface and the sleeve being shaped to receive the hammer toe and cover a substantial portion of the toe.

27 Claims, 6 Drawing Sheets

ORTHOPEDIC TOE DEVICE

This application claims priority to provisional patent application Ser. No. 61/597,245 filed on Feb. 10, 2012, which is incorporated by reference herein.

The invention of this application relates to orthopedic toe products and, more particularly, to a hammer toe treatment device.

BACKGROUND OF THE INVENTION

Hammer toes are a type of foot deformity that affect people worldwide and have for many years. This type of foot deformity results in the curling in and/or under, of one or more toes. This deformity generally occurs in the second, third and fourth toe but can on occasion occur on the Great (Big) toe and Pinky toe of either right or left foot. An extremely common result of hammer toes is that the second knuckle of the toe rises up as the tip of the toe curls in and under it (the second knuckle). This deformity causes the tip of the toe and the top of the second knuckle to be pressed into and rub against the top and the bottom of the inside of a shoe. This often results in the development of corns, calluses or other pressure related sores that cause discomfort and pain and in some cases can be debilitating and impact quality of life.

There are a number of existing products that treat the curling in symptom of a hammer toe. One common product design is called a Hammer Toe Crest Pad. Hammer Toe Crest Pads are somewhat crescent (or more accurately, eye brow) shaped cushioned pads that go under the toes and have an adjustable band or non adjustable loop that allow it to be worn on the toe.

Historically, Hammer Toe Crest Pads have been made from a variety of materials including foam and elastic combined with cloth or leather. Hammer Toe Crest Pads are still made from these materials but contemporary designs also include construction from various types of gel polymers.

Hammer toe crest pads affect correction by pushing or wedging the curling toe open. This helps to reduce contact on the tip of the toe and the top of the second knuckle but it does not eliminate it. By the nature of the design and function of the hammer toe pad and of the effect of the hammer toe deformity itself, the toe will remain in a semi curled position. Since the toes remain in a semi curled position, contact between the interior of a given shoe and the tip of the toe or top of the second knuckle (of the deformed toe) is often not eliminated. As a result, corns, calluses and other pressure related sores do persist. Current designs of hammer toe crest pads do not effectively address the problems caused by pressure from a shoe.

In order to hold the hammer toe crest pad in place, some pads includes a ring that is intended to be positioned over one of the user's toes. Since the typical hammer toe crest pad are not designed to protect a specific toe (or toes) of the user, the location of the attachment ring on the crest pad has not been consequential and has generally been placed in the middle of the hammer toe crest pad. Further, these rings can be uncomfortable and can create unwanted pressure points on the toes.

In addition, there are products that exist to treat corns, calluses and other pressure related sores on the toes. These products are known as toe sleeves and toe caps. Toe sleeves are tubes that are open at both ends like a very short drinking straw and toe caps are open at one end but closed at the other like a small sock or finger condom. Historically, both toe caps and toe sleeves have been made out of foam but modern designs utilizes various gel polymers. Toe caps and toe sleeves do a good job of protecting the toes against corns, calluses and other pressure related sores but in the case of a hammer toe they do nothing to help straighten the toe or help to prevent the advancement of the hammer toe deformity.

In view of the industry shortcomings to completely address the needs of those with hammer toes, applicant considered many possible devices to overcome these shortcomings including combinations of existing devices. However, these attempts were unsuccessful and even potentially dangerous to the user. These shortcomings including combinations wherein combined structures created pressure points that could create excessive pressure on the toe such that blood flow to the toe could be adversely reduced and lead to serious medical problems. Further, these stress points also created excessive strain on the components leading to premature product failure and breakage in the field.

As a result, a product was still needed that would not only uncurl the toe and protect the tip of the toe and the top of the second knuckle from problems resulting from continual pressure and rubbing on the inside of a shoe but will also be safe and not create further medical problems or reduce the durability or life expectancy of the product.

SUMMARY OF THE INVENTION

The present invention relates to orthopedic toe products and, more particularly, to a hammer toe treatment device. In particular, to hammer toe crest pad that incorporates, in a single piece construction, a toe cap or sleeve that completely or partially covers the toe (including the tip of the toe and/or the second knuckle of the toe) and has a crescent shaped pad that goes under the toe perpendicular to the plane of the toe cap or sleeve. This invention of this application both helps to uncurl the toe and protect the areas of the toe that are prone to injury from pressure and rubbing.

More particularly, provided is a hammer toe treatment device to both help uncurl a hammer toe and protect the areas of the hammer toe that are prone to injury from pressure and rubbing, the device comprising a base pad having a shape configured to extend in a neck portion of an associated hammer toe between a corresponding toe mound and corresponding tip portion of the associated hammer toe, the base pad including a top surface with an arcuate surface portion extending in the direction of the associated hammer toe and configured to in part produce a straightening force against the associated hammer toe, the base pad further including a bottom surface portion generally opposite to the top surface, the bottom surface including a generally flat surface portion, the flat surface portion configured to be directly or indirectly engaged by an associated insole of an associated shoe when the associated shoe is worn to provide an upward support force for the straightening force against the associated hammer toe, the base pad further including a length generally transverse to the associated hammer toe, the device further comprising a tubular toe sleeve fixed relative to the base pad and extending forwardly along a sleeve axis from a reward toe opening, the sleeve axis extending at a sleeve angle relative to the bottom surface portion of the base pad, the sleeve being shaped to receive the associated hammer toe and having a length to cover a substantial portion of the associated hammer toe thereby protecting the areas of the hammer toe that are prone to injury from pressure and rubbing.

This design offers hammer toe suffers a more complete, noninvasive (non-surgical) solution to the problems associated with the hammer toe deformity. This design not only helps to straighten the inward curling hammer toe but also helps to protect the toe and aid in the healing as well as prevent the development of corns, calluses or other pressure related sores that cause discomfort and pain and in some cases can be debilitating and impact quality of life. Yet further, the pad and sleeve work in combination with one another to increase the straightening of the hammer toe.

This design also offers consumers a more durable alternative to conventional hammer toe crest pads. All conventional hammer toe crest pads, without exception, have an inherent weak point that inevitably fails and when it fails it renders the crest pad unusable. That weakness is the ring that holds the crest pad to the toe. Conventional crest pads, without exception, have a narrow ring that secures the pad to the toe. Continual strain from wear (walking or running) combined with stretching that is a necessary part of putting the crest pad on the toe and taking it off, weakens the ring to the point where it tears. Once the ring tears the crest pad won't stay in place and replacement becomes necessary. This design improves upon previous designs because the tube atop the crescent shaped pad provides a wider (or longer) and therefore more and durable attachment point to the foot (toe) thereby increasing the overall longevity of the hammer toe treatment product while also improving the performance of the device.

According to another aspect of the present invention, provided is a toe sleeve with a downward toe sleeve angle since toes (even healthy toes) have a slightly downward angle to them. In a hammer toe this downward angle is exaggerated. For anatomical form and overall comfort for the wearer, this new hammer toe sleeve angle provides a more effective function and a distinct appearance.

According to yet other aspects of the present invention, provided is a reward toe opening that is angled such that the bottom portion of the opening is spaced from the webbing.

These and other objects, aspects, features and advantages of the invention will become apparent to those skilled in the art upon a reading of the Detailed Description of the invention set forth below taken together with the drawings which will be described in the next section.

BRIEF DESCRIPTION OF THE DRAWINGS

The invention may take physical form in certain parts and arrangement of parts, a preferred embodiment of which will be described in detail and illustrated in the accompanying drawings which form a part hereof and wherein.

DESCRIPTION OF PREFERRED EMBODIMENTS

Referring now to the drawings wherein the showings are for the purpose of illustrating preferred and alternative embodiments of the invention only and not for the purpose of limiting the same, FIGS. 1-7 shown is an orthopedic toe device 10 according to certain aspects of the invention of this application. However, it must be noted that this device is shown as a device configured to the left foot, but this application is not to be limited to a left footed device only wherein the device of this application can be equally utilized on either foot. But, as can be appreciated, the configuration if the device for the right foot would be generally a reverse of the device shown in the drawings of this application. Yet further, while the devices of this application are shown with respect to a particular toe, the device of this application could be configured for use on any toe and on either foot without detracting from the invention of this application.

Orthopedic toe device 10 is formed by a short tubular structure or toe sleeve 12 mounted or fixed relative to a base pad 14. As will be discussed more, base pad 14 can be a crescent shaped pad and sleeve 12 and pad 14 can be a single molded product. The toe sleeve extends from a first end 20 to a second end 22. Tubular structure 14 further includes a reward opening or toe opening 26 on end 20 and can either include an open or closed end on front or second end 22. Base pad 14 can be shaped roughly like an eyebrow, meaning that it is wider and taller at a medial end 30 and narrower and shorter at a tail or lateral end 32. The base pad has an over all curved or arc configuration along its length 34 and is arcuate in the direct of the user's toes wherein the base pad further includes an arcuate surface portion 40 opposite of a base surface 42. The arced configurations can vary without detracting from the invention of this application and can be designed for specific applications.

The toe sleeve is mounted atop the base pad at any location along length 34 depending on the toe to be corrected. As is shown, toe sleeve 12 is located nearer to medial end 30 wherein it is medially offset from the middle of the base pad.

Tubular structure or toe sleeve 12 is a hollow sleeve formed at least in part by a wall 50 and extends inwardly from reward opening 26 along a sleeve axis 52 toward end 22. Sleeve 12 is configured or shaped to receive a toe T of the user's foot. The sleeve can be a cylindrical sleeve having a generally uniform inner diameter 56. However sleeve 12 could have other configuration without detracting from the invention of the application. For example only, wall 50 could be conical or tapered in configuration and the conical or tapered configuration could be tapered toward end 22 such that end 22 is smaller then end 20 or opening 26. The wall thickness of wall 50 the tubular structure can range and this range can depend on several factors including the intended straightening affect of the sleeve itself that can be in addition to the base pad and the material(s) that are use to product the sleeve. In one embodiment, the wall thickness of wall 50 is between $1/16^{th}$ inch and $1/4^{th}$ inch. In a preferred embodiment, the wall thickness of wall 50 is about $1/8^{th}$ inch. Yet further, the wall thickness can vary along axis 52.

Yet further, opening 26 can have a wide range of configurations. These can include a flat or planar opening configuration. In one set of embodiments, this planar opening 26 is angled such that the top of tube 12 extends back further than the bottom of the tube. This is done to accommodate the webbing between the toes and make the fit more anatomically correct. In yet other embodiments (not shown), the opening can be sculpted to accommodate the toe's webbing.

Figures 1, 2, 3, 4:
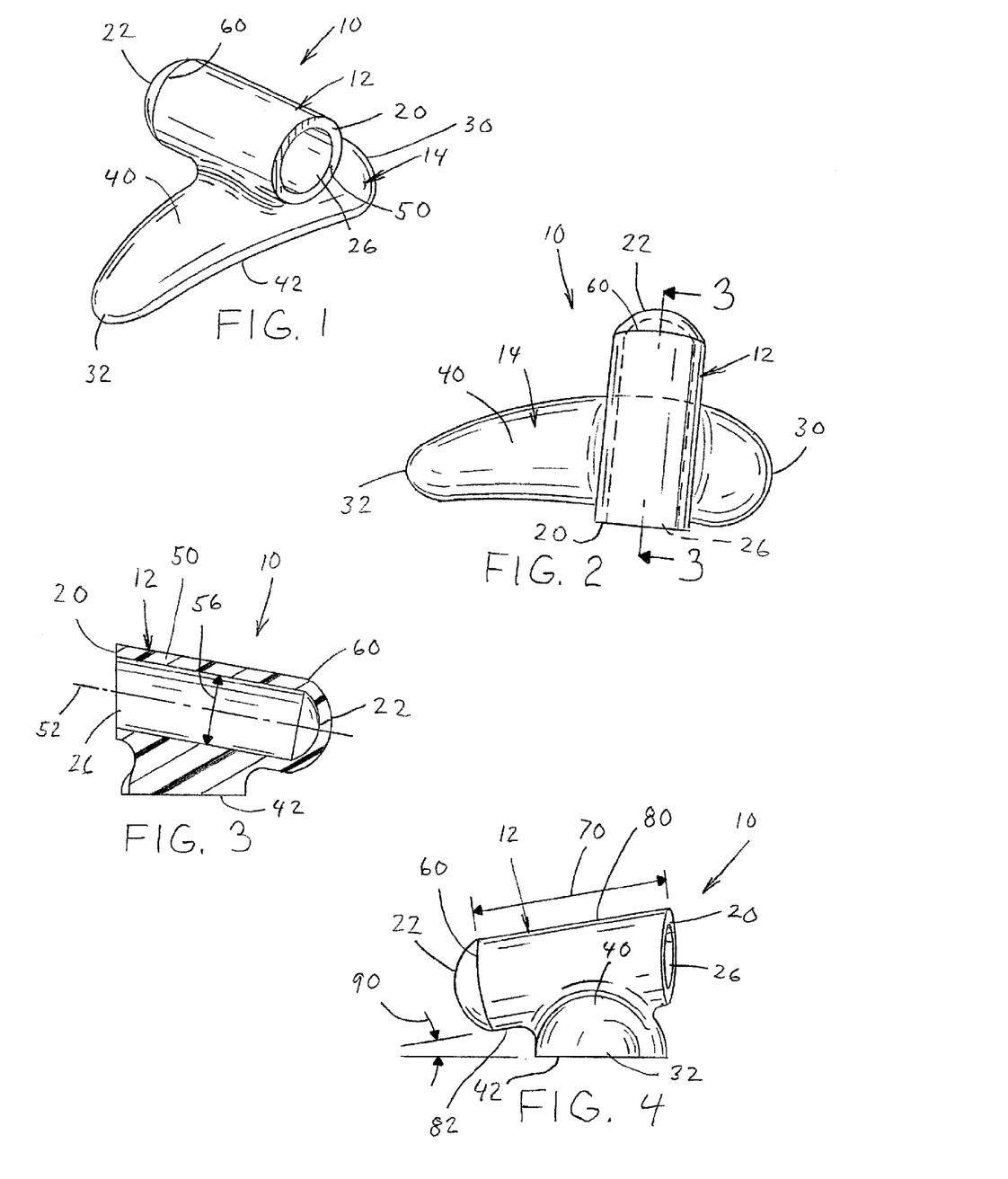
FIG. 1 is a perspective view of an orthopedic toe device according to certain aspects of the present invention shown in relation to a left footed configuration.
FIG. 2 is a top view of the device shown in FIG. 1.
FIG. 3 is a sectional view taken along lines 3-3 in FIG. 2.
FIG. 4 is a left side view of the device shown in FIG. 1.
Figure 5:
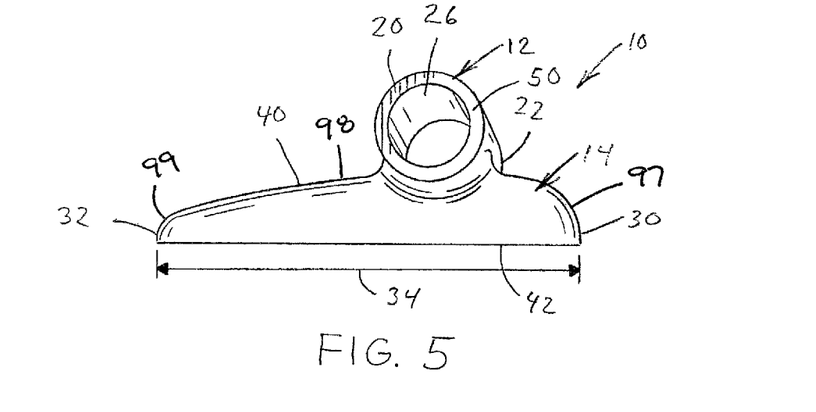
FIG. 5 is a rear side view of the device shown in FIG. 1.
Figure 6:
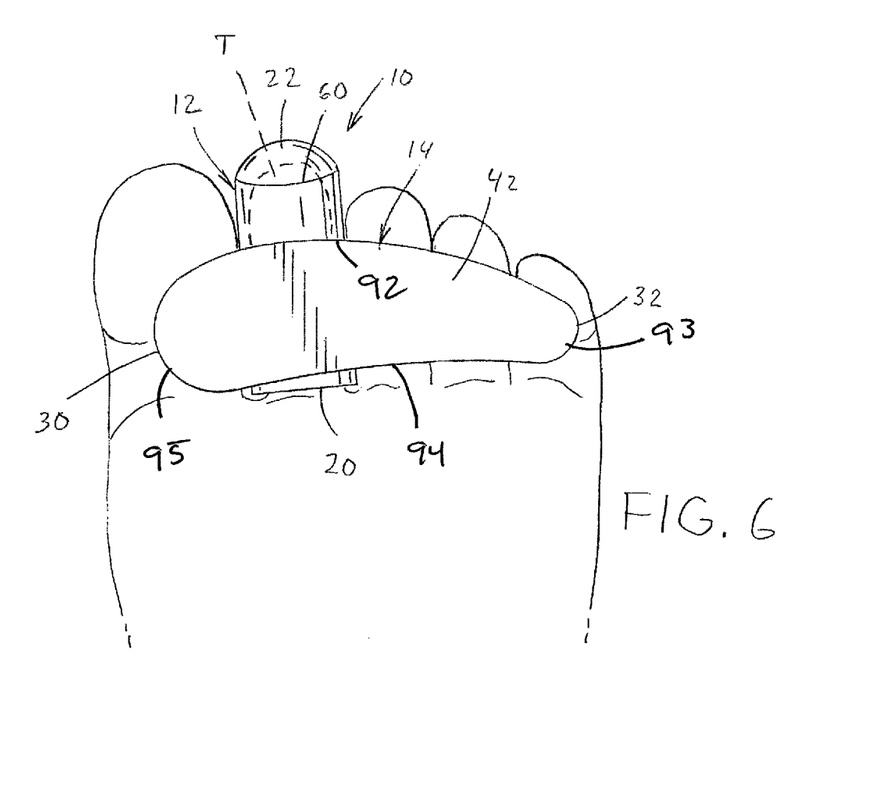
FIG. 6 is a bottom view of the device shown in FIG. 1 shown in place on a user's foot.
Figure 7:
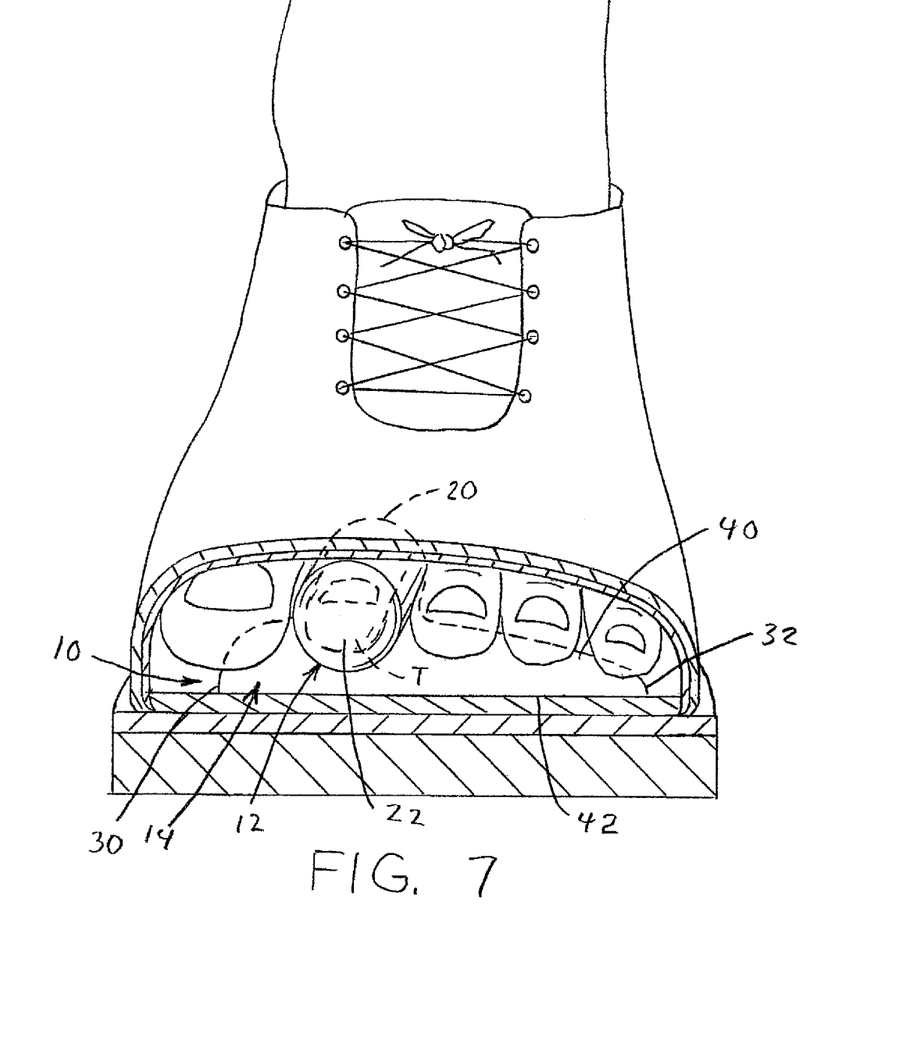
FIG. 7 is an end view of the device shown in FIG. 1 shown in place on a user's foot within a shoe.
Figure 8:
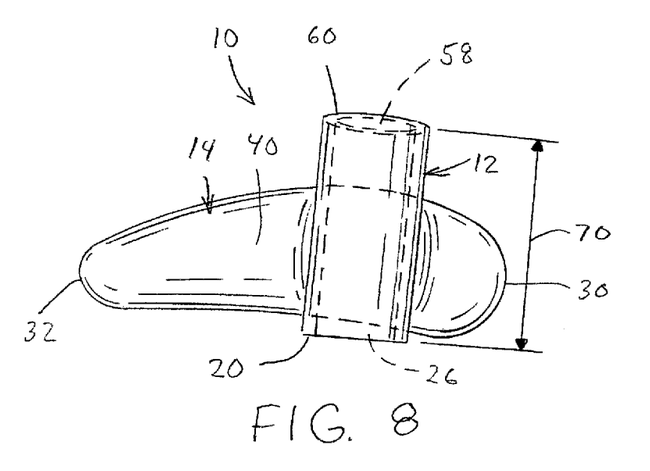
FIG. 8 is a top view of an orthopedic toe device according to certain other aspects of the present invention again shown in relation to a left footed version of the device.
Figure 9:
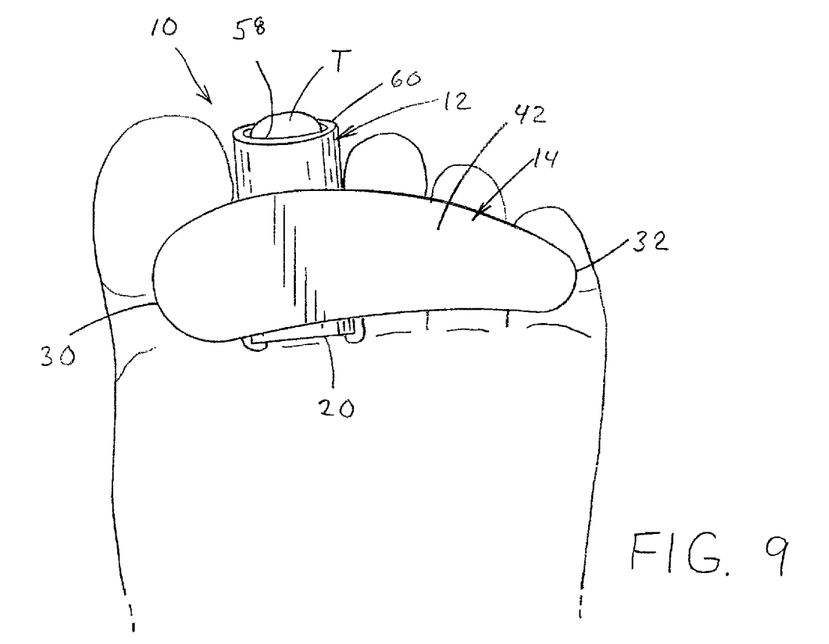
FIG. 9 is a bottom view of the device shown in FIG. 8 shown in place on a user's foot.
Figure 10:
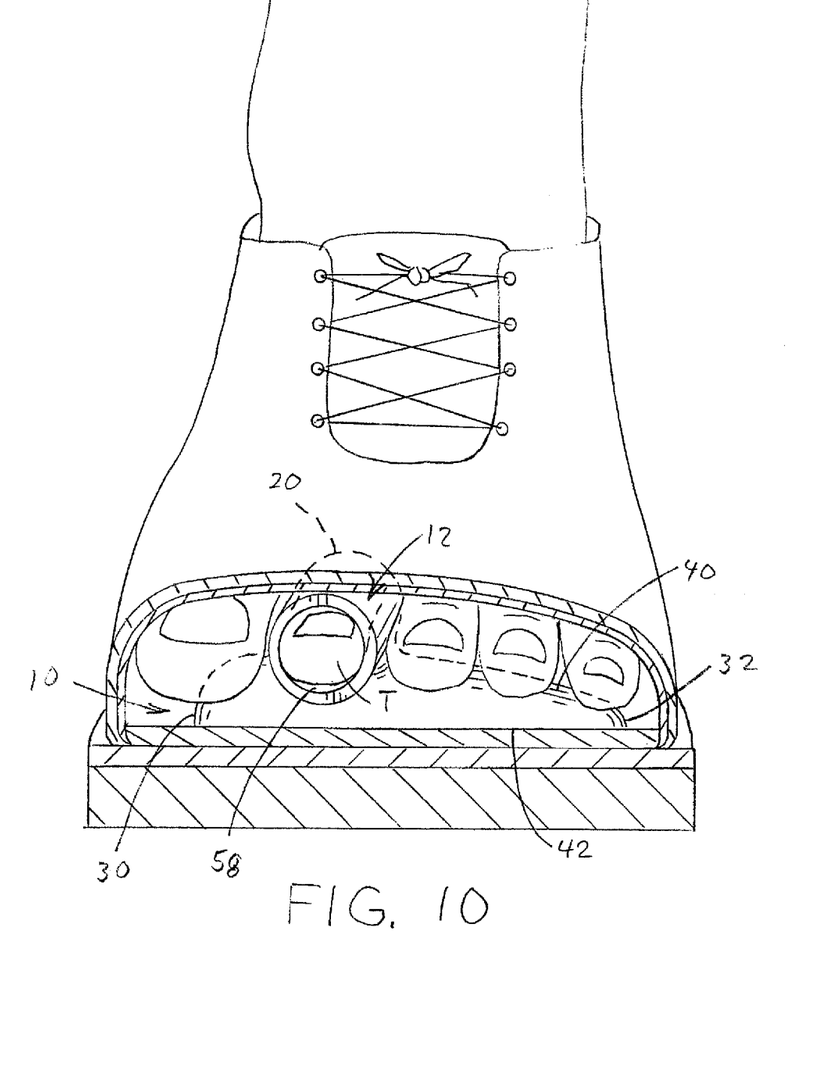
FIG. 10 is an end view of the device shown in FIG. 8 shown in place on a user's foot; and, FIG. 11 is a top view of another orthopedic toe device according to other aspects of the present invention shown in relation to a left footed configuration.

End 22, which is referred to as the front end, can also have different configurations. According to one embodiment, end 22 can be an open end such that toe sleeve 12 is open at both ends with a front end opening 58 as is shown in FIG. 8. According to another embodiment, end 22 can be a closed end to form a cap like design. Yet further, sleeve 12 can include a cutting line 60 such that the end user can modify the sleeve to change a closed sleeve into a sleeve having opening 58. Cut line 60 could be any type of cut line including, but not limited to, a molded groove, a molded ridge and a printed line, and could be continuous about axis 52 or non-continuous (such as a dashed line). As with opening 26, opening 58 can be a planar opening and can be perpendicular to axis 52 and wall 50. In yet other embodiments, opening can be angled greater or less than 90 degrees from axis 52. With respect to the closed cap configuration, the end of tube 12 can have a wide range of configurations including a nearly flat end, a hemispherical end and a rounded shape. As can be appreciated, this end shape can vary based on the configuration of wall 50.

Sleeve 12 also includes a length 70 that can extend between ends 20 and 22 or as shown extend between end 20 and cut line 60 or end 58. Further, as with inner diameter 56, length 70 can vary depending on a wide range of factors including, but not limited to the size of the user's toes and the materials used. For example, the device of this application can come in multiple sizes such as small, medium and large sizes. The dimension of length 70 and diameter 56 can also vary based on which toe the device is intended to correct, such as depending on whether sleeve 12 is configured to be positioned on the second toe, third toe, or fourth toe. Yet other considerations for sizes are whether the tube 12 is an opened or a closed configuration. In this respect, tube length 70 can range from about 0.5 inches to about 2 inches long. In a preferred embodiment, length 70 is about 1.5 inches. Yet further, and as is referenced above, length 70 for a top portion 80 tube 12 can differ slightly from length 70 of a bottom portion 82 of tube 12 depending on the anatomical angling of the back side of the tube (open insertion end for the toe) and/or any front side angling of opening 58. In addition, inner dimension (diameter in certain embodiments) can also vary based on the size of the toes and the toe that sleeve 12 is configured to interengage with. Thus, dimension 56 can range from about $3/8^{th}$ inch to about $5/8^{th}$ inch wide. In a preferred embodiment, the dimension 56 is about ½ inch.

In addition, sleeve 12 is configured to set atop of pad 14 and pad 14 is configured to fit within the neck portion of the toes and can be crescent shaped. However, pad 14 could be other shapes and could be limited in length to only engage the toe to be corrected. Further, sleeve 12 can be at an angle relative to pad 14. In this respect, device 10 further has a sleeve angle 90 relative to bottom surface portion 42 and axis 52. This angle can range from 0.0 degrees to 20 degrees. In others embodiments, sleeve angle 90 is between 5 degrees and 20 degrees. In another set of embodiments, angle 90 is between 5 degrees and 15 degrees and it is preferred that angle 90 is about 10 degrees. As is shown, these angles are such that tube or sleeve 12 is tilted to a forward and downward angle. This can be done to improve comfort and/or fit by better accommodating the anatomical shape of a curling hammer toe.

Sleeve 12 can be joined to base pad 14 by any means known in the art including a unified molded device 12. The fit between sleeve 12 and pad 14 can include a fillet design that smoothly blends the walls of the tube with the body of the base pad. This adds structural integrity to the over all design (to the connection point between the tube element and the crescent element). The Tube is inset slightly into the body of the crescent shaped pad (rather than sitting directly on top of it). This can be done for structural integrity as well as to create a more anatomical shape for comfort and functionality.

The positioning of sleeve or tube 12 can be offset from the center to the medial side of the crest pad by a distance that can vary depending on size embodiment (small, medium or large or second toe, third toe, fourth toe) but is preferably set toward medial end 30. This has been found to be an element of the invention of this application since this product is designed to both uncurl and protect a specific toe.

As discussed above, shape of based 14 can be similar to the shape of an eyebrow with medial end 30 having a higher volume (wider, taller and more rounded) which tapers down to lateral end 32 which has a lower volume (narrower, lower and more pointed). The most effective part of a hammer toe crest pad for uncurling a toe is the thicker medial side of the pad. This is because the higher volume medial end puts more material under the curling toe which pushes it open to a greater degree. Since the ring on a conventional hammer toe crest pad does nothing to protect and/or uncurl the toe and is there solely to keep the apparatus attached to the foot, the attachment ring has always been centered in the middle of the crest pad. The user can then wear the hammer toe crest on either the second, third or fourth toe choosing the configuration that puts the thicker medial end under the affected toe.

By utilizing an offset design, it has been found that the thicker medial end (the most effective end for uncurling the toe) can be positioned under the affected toe thereby improving the effectiveness of the toe treatment product.

The maximum height of the crescent shaped pad can vary depending on size embodiment (small, medium or large or second toe, third toe, fourth toe) and can preferably range from about $3/8^{th}$ inch up to about $5/8^{th}$ inch. In any case the maximum height of the crescent shaped pad tapers down in all directions from the top of the pad to the front, back medial and lateral side at different rates and different degrees.

The maximum width of the crescent shaped base pad also can vary depending on size embodiment (small, medium or large or second toe, third toe, fourth toe) and can preferably range from about ½ inch up to about 1 inch. In any case the maximum width of the crescent shaped pad tapers down in all directions from the top of the pad to the front, back medial and lateral side at different rates and different degrees.

Length 34 of base pad 14 can vary depending on size embodiment (small, medium or large or second toe, third toe, fourth toe) and can preferably range from about 2 inches up to about 3.5 inches. In a preferred embodiment, it is about 2.95 inches. The width of based pad 14 can be about 1 inch in a preferred embodiment.

Similarly, the shape of base pad 14 is preferably arcuate and formed by a plurality of curvilinear sections that can have uniform curved portions and/or varying curved portions generally configured to maximize both comfort and corrective properties. As can be appreciated, it is preferred that adjacent curvilinear sections flow into one another thereby reducing both stress points in the product and stress points in the products interaction with the user's foot. Thus, these radii can and do vary wherein the dimensions below are given in ranges and the actual curves could have many varying dimension along these curves. With respect to the preferred embodiment shown in the drawings, base pad 14 has four general blended curves defining bottom surface 42 and/or the bottom in general. These include curved portions or edges 92-95 wherein portion 92 can have a curvature dimension or dimensions in the range of about 0.025 inches to 0.20 inches; portion 93 can have a curvature dimension or dimensions in the range of about 0.20 inches to 1.20 inches; portion 94 can have a curvature dimension or dimensions in the range of about 0.01 inches to 0.20 inches; and portion 95 can have a curvature dimension or dimensions in the range of about 0.20 inches to 0.60 inches. Similarly, top portion 40 of base pad 14 can have a wide range of curvilinear portions and can include curved portions or surfaces 97-99. Portion 97 can have a curvature dimension or dimensions in the range of about 0.05 inches to 0.20 inches; portion 98 can have a curvature dimension or dimensions in the range of about 0.0 inches to 0.20 inches; and portion 99 can have a curvature dimension or dimensions in the range of about 0.05 inches to 0.50 inches.

However, while all of the dimensions of this application represent preferred embodiments, the invention of this application is not to be limited to these dimensions unless specifically claimed and can take on different forms and dimensions without detracting from the invention of this application. This is especially true for the several different sizes of the invention of this application in view of different foot and toe sizes of the end user.

While it has been found that a range of materials can be used, it is preferred that the hammer toe device be made from a gel material.

Yet further, even though the hammer toe device is preferably a single piece design, the invention of this application is not to be limited to a device that is a single molded article. The invention includes configurations wherein multiple molded articles are joined together by any method known in the art.

Figure 11:
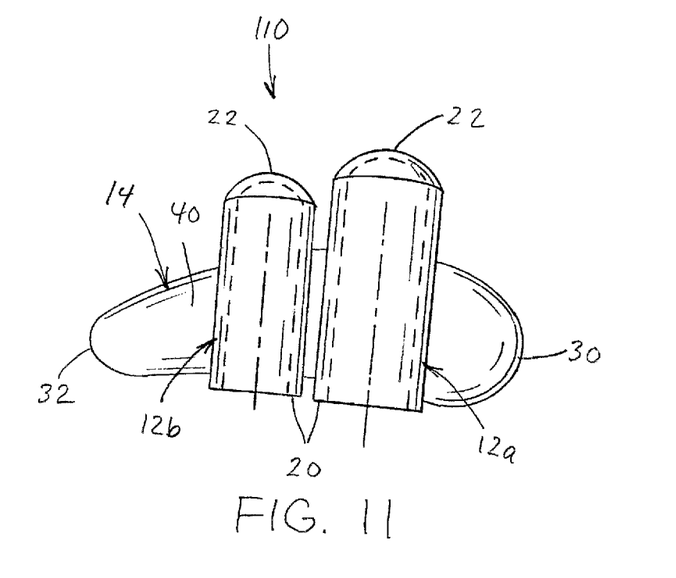

Even yet further, and with special reference to FIG. 11, the invention can include devices that include more than one sleeve and/or cap fixed relative to the crest pad such that the base crest pad could have multiple caps and/or sleeves attached to it in the same way as the single one shown in the drawings. As is shown, device 110 includes a similar base pad 14 and includes two toe sleeves 12a and 12b. The pads and sleeves of these embodiments can include any of the configuration and features described in this application without detracting from the invention of this application.

While considerable emphasis has been placed on the preferred embodiments of the invention illustrated and described herein, it will be appreciated that other embodiments, and equivalences thereof, can be made and that many changes can be made in the preferred embodiments without departing from the principles of the invention. Furthermore, the embodiments described above can be combined to form yet other embodiments of the invention of this application. These include various fluid flows to drive the motor. Accordingly, it is to be distinctly understood that the foregoing descriptive matter is to be interpreted merely as illustrative of the invention and not as a limitation.

It is claimed:

1. A hammer toe treatment device to both help uncurl a hammer toe and protect the areas of the hammer toe that are prone to injury from pressure and rubbing, the device comprising a base pad having a shape configured to extend in a neck portion of an associated hammer toe between a corresponding toe mound and corresponding tip portion of the associated hammer toe, the base pad including a top surface with an arcuate surface portion extending in the direction of the associated hammer toe and configured to in part produce a straightening force against the associated hammer toe, the base pad further including a bottom surface portion generally opposite to the top surface, the bottom surface including a generally planar surface portion, the planar surface portion configured to be directly or indirectly engaged by an associated insole of an associated shoe when the associated shoe is worn to provide an upward support force for the straightening force against the associated hammer toe, the base pad further including a length generally transverse to the associated hammer toe, the device further comprising a tubular toe sleeve fixed relative to the base pad and extending forwardly along a sleeve axis from a reward toe opening, the sleeve axis extending at a sleeve angle relative to the bottom surface portion of the base pad and the sleeve angle being greater than 5 degrees, the sleeve being shaped to receive the associated hammer toe and having a length of greater than 0.5 inches to cover a portion of the associated hammer toe thereby protecting the areas of the hammer toe that are prone to injury from pressure and rubbing.

2. The hammer toe treatment device of claim 1, wherein the sleeve angle is between 5 degrees and 20 degrees.

3. The hammer toe treatment device of claim 2, wherein the reward opening is generally perpendicular to the bottom surface of the base pad.

4. The hammer toe treatment device of claim 1, wherein the sleeve angle is between 5 degrees and 15 degrees.

5. The hammer toe treatment device of claim 4, wherein the reward opening is generally perpendicular to the bottom surface of the base pad.

6. The hammer toe treatment device of claim 4, wherein the sleeve angle is about 10 degrees.

7. The hammer toe treatment device of claim 4, wherein the reward opening is angled at a forward angle such that a top portion of the opening extends reward of a bottom portion of the opening.

8. The hammer toe treatment device of claim 1, wherein the reward opening is generally perpendicular to the bottom surface of the base pad.

9. The hammer toe treatment device of claim 1, wherein the sleeve length is greater than 1.5 inches.

10. The hammer toe treatment device of claim 1, wherein the sleeve has an inside diameter and the inside diameter is greater than 0.5 inches.

11. The hammer toe treatment device of claim 1, wherein the sleeve further includes forward opening opposite of the reward opening.

12. The hammer toe treatment device of claim 1, wherein the sleeve extends between the reward opening to a front extent, the front extent being closed off.

13. The hammer toe treatment device of claim 1, wherein the reward toe opening is reward of the base pad.

14. The hammer toe treatment device of claim 1, wherein the sleeve further includes a front end opposite of the reward opening, the front end extending forward of the based pad.

15. The hammer toe treatment device of claim 1, wherein the base pad is crescent shaped and extends between a first and a second end defining the length of the base pad, the first end being wider in the toe direct than the second end, the sleeve being positioned off center between the first and second ends.

16. The hammer toe treatment device of claim 15, wherein the sleeve is positioned near the first end.

17. The hammer toe treatment device of claim 1, wherein the base pad and the tubular toe sleeve are a single molded article.

18. The hammer toe treatment device of claim 1, wherein the sleeve angle is between 5 degrees and 15 degrees, the reward opening is angled at a forward angle such that a top portion of the opening extends reward of a bottom portion of the opening, the sleeve length being greater than 0.75 inches.

19. The hammer toe treatment device of claim 18, wherein the sleeve further includes forward opening opposite of the reward opening.

20. The hammer toe treatment device of claim 18, wherein the sleeve extends between the reward opening to a front extent, the front extent being closed off.

21. The hammer toe treatment device of claim 18, wherein the reward toe opening is reward of the base pad.

22. The hammer toe treatment device of claim 18, wherein the sleeve further includes a front end opposite of the reward opening, the front end extending forward of the based pad.

23. The hammer toe treatment device of claim 18, wherein the reward toe opening is generally perpendicular to the bottom surface of the base pad.

24. The hammer toe treatment device of claim 18, wherein the base pad is crescent shaped and extends between a first and a second end defining the length of the base pad, the first end being wider in the toe direct than the second end, the sleeve being positioned off center between the first and second ends.

25. The hammer toe treatment device of claim 24, wherein the sleeve is positioned near the first end.

26. The hammer toe treatment device of claim 1, wherein the sleeve is inset into the base pad and the arcuate surface portion.

27. The hammer toe treatment device of claim 1, wherein the sleeve is a first sleeve, the device further including a second sleeve for a second hammer toe.

\* \* \* \* \*